United States Patent [19]

Braun et al.

[11] 4,116,200

[45] Sep. 26, 1978

[54] MILLING TOOL FOR SURGICAL PURPOSES

[75] Inventors: Karl Braun, Talheim; Rainer Lacher, Muhlheim; Willi Pfeiffer, Tuttlingen, all of Germany

[73] Assignee: Aesculap-Werke Aktiengesellschaft vormals Jetter & Scheerer, Tuttlingen, Germany

[21] Appl. No.: 728,728

[22] Filed: Oct. 1, 1976

[30] Foreign Application Priority Data

Oct. 1, 1975 [DE] Fed. Rep. of Germany ....... 2543723

[51] Int. Cl.$^2$ ............................................. A61B 17/32
[52] U.S. Cl. ........................................ 128/305; 29/78; 30/276; 30/279 R
[58] Field of Search .................... 128/305, 2 B, 305.1; 29/78; 30/276, 279 R; 76/101 A

[56] References Cited

U.S. PATENT DOCUMENTS

| 3,633,583 | 1/1972 | Fishbein | 128/305 |
| 3,667,456 | 6/1972 | Charnley | 128/305 X |
| 3,702,611 | 11/1972 | Fishbein | 128/305 |

FOREIGN PATENT DOCUMENTS

| 2,500,958 | 7/1976 | Fed. Rep. of Germany | 128/305 |
| 166,449 | 1/1965 | U.S.S.R. | 128/305 |

*Primary Examiner*—Robert W. Michell
*Assistant Examiner*—Michael H. Thaler
*Attorney, Agent, or Firm*—Wigman & Cohen

[57] ABSTRACT

A surgical milling tool with a hand-operated milling machine for milling the heads or sockets of bone joints of spherical shape is disclosed. The tool is formed of a hemispherical cup integrally formed with a cylindrical skirt and flange and is provided with a plurality of openings of semi-oval shape, each having a cutting edge arranged at the minor axis of the oval shape. The openings are situated such that, upon rotation of the cup, the cutting edges thereof overlap to provide a continuous cutting edge surface conforming generally to the shape of the cup.

10 Claims, 5 Drawing Figures

MILLING TOOL FOR SURGICAL PURPOSES

The invention consists of a milling tool for surgical purposes, designed to mill heads or sockets of joints of spherical form, which comprises a cup formed at least partly as a half sphere and in any case can be connected with a hand-operated milling machine to revolve around the axis of the sphere which is perpendicular to the equatorial plane of the half sphere, the milling tool being equipped with openings. During the rotation of the cup, the edges which follow in sequence around the rotation axis of the hand-operated milling machine form sharp edges on the surface of the cup. The tangents of the sharp edges fit close to the angle at the point of intersection with the circular trajectory of these end points.

In the case of the known milling tools of this kind, the edges form grate-like teeth. With such grate-like teeth, similar to those used for peeling potatoes; only the tips of the teeth do the cutting. For that reason it is impossible in the case of the known milling tool to peel off evenly the head of the bone joint evenly and thereby produce an accurate spherical shape. In working on the top of a hip, the known type of milling head shifts frequently and rattles to the side with the different degree of hardness of the bone, or also in the case of a partly unrounded form of the top of the hip which has been deformed because of sickness. Because of the "tearing down" of individual teeth during the milling process, the milling tool could stop the operation with a jerking motion, and as a result more bone could be cut out than desired. That is why it is not possible to do precision working for example on the top of a hip bone with the required accuracy of a few tenths of a millimeter, when one uses a milling tool with such grate-like teeth.

Another disadvantage of the known milling tools of this type is the fact that the shaving consists of pieces of cartilage and more or less fine bone dust. After working on the head of a joint or the socket of a joint, the shavings and the bone dust must be removed from the area of the operation, and especially they must be brushed off the head of the joint, or washed out of the socket of the joint. But it is in practice impossible to remove the shavings entirely, especially the fine bone dust. Bone dust which remains in the wound caused by the surgical operation may affect subsequent induration of the tissue of the newly formed articular capsule.

SUMMARY AND OBJECTS OF THE INVENTION

The purpose of the invention is to create a milling tool for surgical purposes, by which one can avoid the formation of fine shavings and especially fine bone dust.

This problem is solved in the case of a milling tool of the type described at the beginning according to the invention in the following way: all the cutting edges of the milling tool are formed by the openings of the edges running in sequence, so that at least those cutting edges with a distance from the rotating axis smaller than the radius of the flat surface of the half-sphere run essentially over the entire length of the cutting edges which remain at the same distance from this flat surface of the sphere, and so that the openings on the half-sphere are distributed and set axially in such an order with regard to each other that the rotating trajectory of the cutting edges cover the entire surface of the half-sphere. As a result of the fact that the cutting edges of the milling tool, which are formed of openings through the edges which follow in sequence, run over the entire length of the opening at an equal distance from the surface of the sphere of the outside surface, each cutting knife operates as a peeling knife, which peels a shaving which can be deflected through the opening, so that it breaks only when it reaches a relatively great length. This prevents the formation of bone dust or other small shavings. As a result of the fact that the openings on the sphere are so distributed and axially set in arranged positions with regard to each other that the rotating paths of the cutting knives cover the entire surface of the half sphere, the cutting knives can be made relatively short and set in such a way that they peel actually the same clean and long shavings. But at the same time the result is that in spite of the relatively short cutting knife in relation to the circumference of the half sphere the entire surface of the sphere is shaved at the same time without the necessity of jerking the milling tool. As a result, one can peel in a spherical shape for example the top of a hip by pushing the milling tool axially on the top of the joint.

The distance of the cutting knife, at which these cutting knives are running on the outside of the flat surfaces of the sphere, can be selected in such a way that the rattling can be definitely prevented. In a preferred example of the design, this distance amounts to a fraction of a millimeter, preferably less than 0.3 millimeters.

A good discharge of shavings can be achieved in this way by selecting an appropriate angle of the shavings, preferably a shaving angle of about 45°.

In order to prevent the clogging of the openings with shavings, it is advantageous to make sure that the length of the openings, measured in the direction of the rotation, is preferably at least 1.5 times larger than its largest axial width.

In the case of a preferred variation of the invention, the half-sphere or hemispherical cup is provided with a portion which extends beyond the equator of the hemispherical portion of the cup and forms a widened border or flange. This border or flange preferably arches convexly towards the inner side of the cup and extends outwardly therefrom. This example of a design of a milling tool according to the invention can also be pushed in the axial direction on a relatively large and/or deformed head of a joint, for example top of a hip, so that the cutting edges cut off all the excessive parts on the top of the joint at the widened border, while the milling tool is pushed up in the axial direction. The cutting effect of these cutting edges is particularly powerful in the case of a milling tool used for tops of joints, when the enlarged border arches convexly on its inner side, because in that case the convexly arched cutting knives remove thicker shavings.

In the case of a design of the invention which is used advantageously for milling of tops of joints, it has been provided that the cup can be connected in a detachable way with a bell which envelopes it from the outside at a radial distance, and that it points to the connecting end for the detachable connection with the hand-operated milling machine tool. The result of it is that the shavings which have passed through the openings and come out of the milling tool collect in the area between the cup and the bell, and consequently it is not necessary to pick the shavings out of the area of the operation.

As it follows from what was said above, the milling tool according to the invention can be designed both for milling of tops of joints as well as for milling of sockets of joints. In this case, the cutting edges must be arranged simply on the inner flat surface or on the external flat surface of the outside of the milling tool.

The invention is explained in detail on the example of a milling tool presented in the drawings. This type is used for milling of the head of a joint, especially of the head of a hip joint.

DETAILED DESCRIPTION OF A PREFERRED EMBODIMENT

Figure 1:
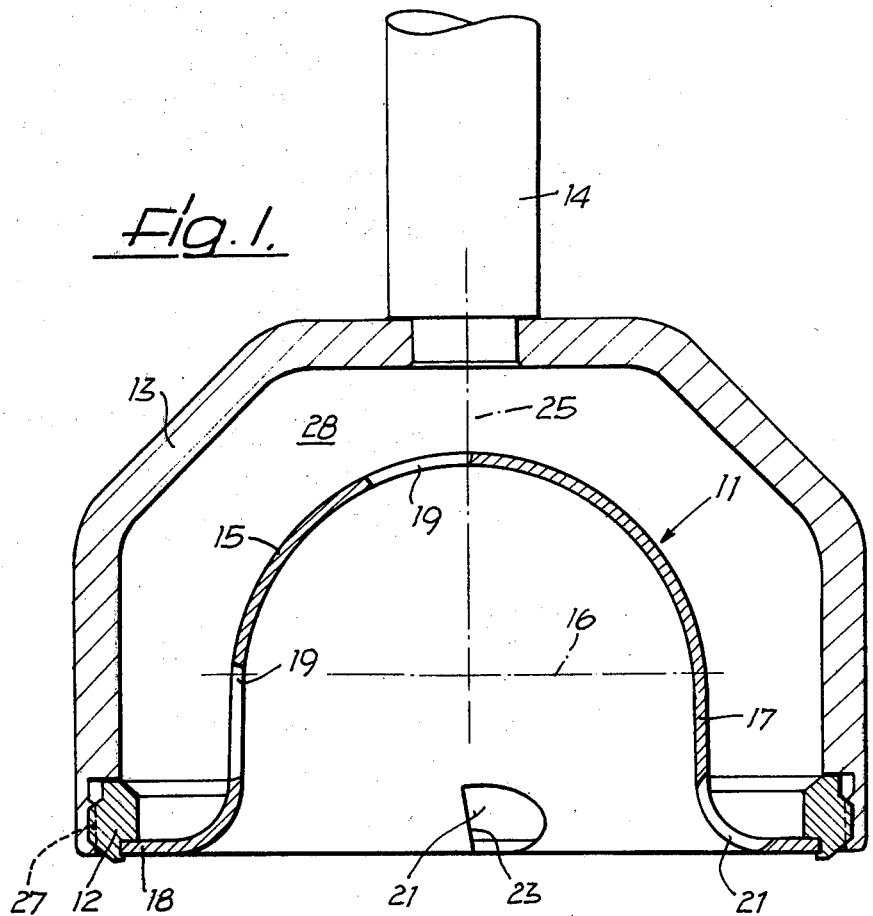
FIG. 1 shows an axial cross section of the example of a design of the milling tool where the shaft is dismantled and given the view from the side, FIGS. 2 and 3 gives the straight view of the outside surface of the tool of an example of the execution of the tool according to FIG. 1, and FIGS. 4 and 5 show the cross sections along the lines IV — IV in FIG. 3 and V — V in FIG. 2, respectively.
Figure 3:
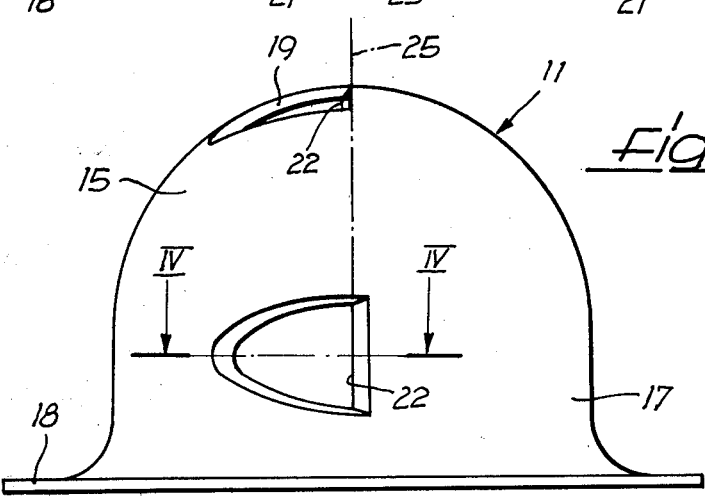

The milling tool for surgical purposes shown in the drawings, which is used for milling heads of bone joints of spherical form, comprises a cup designated generally by reference numeral 11. Cup 11 forms the actual cutting tool, as explained in greater detail below. The cup 11 is connected with a shaft 14 by means of a ring 12 and a bell 13. The shaft is provided for the purpose of connecting the tool with the tool holder of a hand-operated milling machine, which is not shown in the drawing.

The cup 11 is built partly as a hemispherical portion 15, which at its equator 16 shown in FIG. 1 as a dash dotted line, turns into a part which forms first a cylindrical neck 17 and then a border 18 which extends and arches convexly on its inner side facing the inside of the cup 11. The hemispherical portion 15 and the neck 17 of the cup 11 are provided with openings 19 and the border 18 with openings 21. The openings 19 and 21 have the form of a half oval. Because of the half cut of the front view, the end limit of the oval forms a straight line, which runs along the small diameter of the oval on the inner side of the cup 11. These straight-line-limits form cutting edges 22 of the openings 19 and cutting edges 23 of the openings 21.

Figure 2:
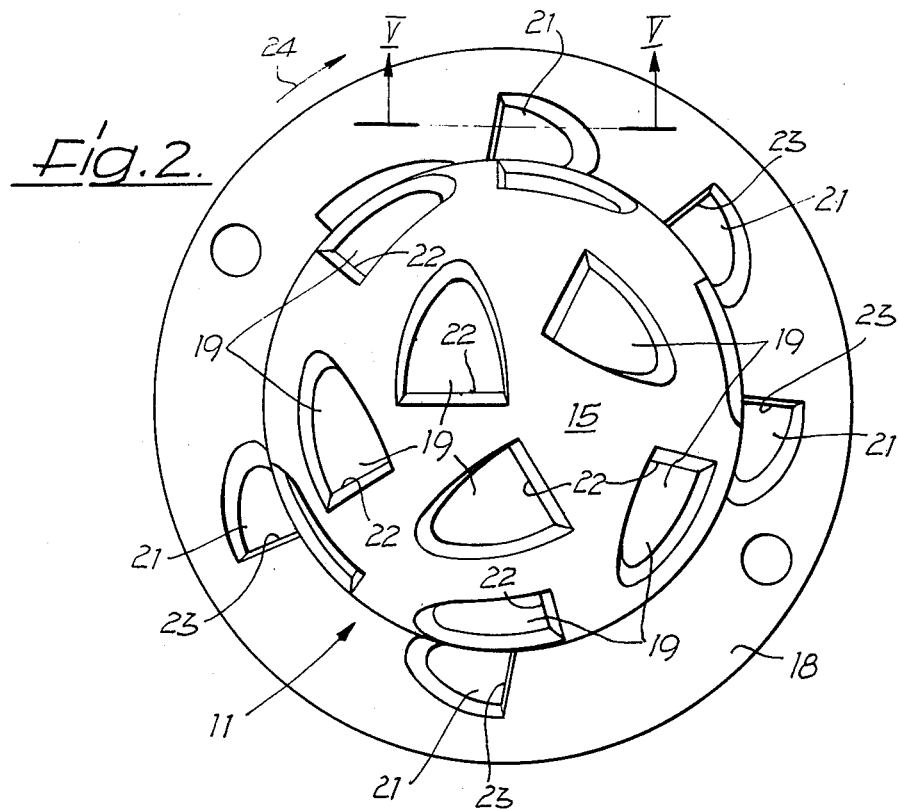
Figure 4:
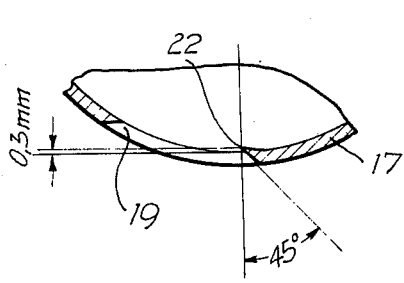
Figure 5:
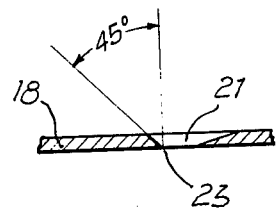

The milling tool as described is designed for rotation in the direction of the arrow 24 in FIG. 2 around the axis of the hemispherical portion 15 which is perpendicular to the plane of the equator 16. The axis of the hemisphere therefore forms the axis of rotation 25 of the milling tool. All the openings 19 and 21 are so arranged that the cutting edges 22 and 23, respectively, follow the appropriate opening when the tool rotates, and that the trajectories of these cutting edges cover the entire inner surface of the hemispherical portion 15, of the neck 17, and of the adjacent inner part of the border 18, as shown in FIG. 2. At the same time, the openings 19 of the hemispherical portion 15 are so arranged that the cutting edges 22 lie in the meridian of the hemispherical portion 15. In addition, the edges of the opening 19, which shows straight lines in the front view, as shown in FIG. 4 are compressed in such a way that the cutting edges 22 run substantially over their entire length at an even distance of about 0.3 millimeters from the inner side of the hemispherical portion 15 and of the neck 17, and as a result they form protruding teeth inside of the hemispherical portion and of the neck. This protrusion of the edges 22 is important particularly for those openings 19 of the hemispherical portion 15 which have a distance from the axis of rotation 25 smaller than the radius of the inner surface of the hemispherical portion, because these cutting edges have a lower rotational speed when the tool rotates around the axis 25, and consequently they have a smaller cutting effect. Yet the cutting edges 23 of the opening 21 in the border 18 lie in the inner surface of the border, so that as a result of the convex arching of the border they have a relatively strong cutting effect anyway. The cutting edges 23 are inclined by an acute angle in relation to axial planes crossing them so that those cutting edges produce a drawing cut when the tool runs. This is an advantage, because these cutting edges have the highest running speed and have to perform the greatest cutting work in the case of deformed or relatively large heads of the joints.

The ring 12 encloses the outermost edge of the border 18 and is fastened to it by soldering or welding. The ring 12 is provided at its perimeter with an external thread 27 for which the free border of the bell 13 shows an inner thread, so that the hemispherical portion 15 can be connected with the bell 13 by screwing. As shown in FIG. 1, the bell 13 and the cup 11 enclose a space 28.

During the process of milling of the head of a joint, for example of the head of a hip, the milling tool described above is pressed axially against the head of the joint, so that the excess parts of the head of the joint which were caused by for example by deformation, are peeled off first of all by the cutting edges 23 of the border 18. As a result, long bone and cartilage shavings are formed and collected in the space 28. When the milling tool continues to be pushed forward, the cutting edges 22 come into action and also peel long shavings, until the head of the joint has a neat spherical form, which turns into a cylindrical part, so that caps can be mounted on the head of a joint which has been worked on in this way, the depth of these caps being greater than the radius of the sphere. Such caps can only rotate on the head of the joint, but they cannot execute any wobbling movement. According to the latest findings of the technique of the operation, this is better than to have wobbling caps. But if it is desirable to work the head of the joint in such a way that it is possible to mount caps which are just as deep as the radius of the sphere, so that the caps can execute a wobbling movement in the mounted position, then the cup 11 must be built in such a way that the border 18 is directly attached to the equator 16. All shavings formed during the working of the head of the joint are collected in the space 28, and this prevents soiling of the field of the operation. If in spite of that a shaving would fall into the field of the operation, then it can be easily found because of its size and taken out. Perfect conducting of the tool is achieved by the spherical surfaces of the hemispherical portion 15 which interconnect and lie between the openings 19.

In the example of the version presented here, the cutting edges 22 and 23 run in the axial planes or in the planes which form a sharp angle with the axial planes, respectively. This by itself is a characteristic which is important for the scaling, namely that the tangents at the end points of the cutting edges with the rotational trajectories of these end points form a right angle or almost a right angle respectively. But the cutting edges do not have to lie unconditionally in these planes. They can be also curved as viewed from above. However, what is important in this respect is the fact that — as explained above — the tangents of the cutting edges form an angle of at least about 45° at their end points with the rotational trajectories of these end points.

The example of the version of the tool describes above shows without any further explanation how it is necessary to build the corresponding tool for milling of the sockets of the joints, for example the acetabulum, for example according to the technique shown in the U.S. Pat. No. 3,605,527, so that it is not necessary to give a description of a corresponding example of the design.

We claim:

1. A surgical milling tool for milling a member of a joint having a substantially spherical shape, said tool being adapted to be connected to a hand-operated milling machine and comprising a cup member having a milling surface, at least a portion of said milling surface being hemispherical, said hemispherical portion being defined by a radius and an equatorial plane, said cup member being rotatable about an axis perpendicular to the equatorial plane, said hemispherical portion having a plurality of openings therethrough, each of said openings having a trailing edge portion on the perimeter thereof, each trailing edge portion defining a cutting edge movable along a cutting trajectory when said cup member is rotated about said axis, at least some of said cutting edges being spaced from said axis of rotation by a distance less than said radius of said hemispherical portion, each cutting edge having a length, the entire length of at least some of said cutting edges being substantially equi-spaced a radial distance from a hemispherical surface of said cup member, said openings being distributed over said hemispherical portion in relation to one another such that the cutting trajectories of said at least some cutting edges define a hemisphere.

2. A surgical milling tool according to claim 1, wherein the rake angle of the cutting edges is about 45°.

3. A surgical milling tool according to claim 1, wherein the length of said at least some cutting edges are spaced from said hemispherical surface a distance less than one millimeter.

4. A surgical milling tool according to claim 1, wherein the length of each opening as measured in the direction of rotation of the cup member is at least 1.5 times greater than the greatest width of such opening as measured axially of the cup member.

5. A surgical milling tool according to claim 1, wherein said cup member includes a flange portion formed adjacent the equator of the hemispherical portion, said flange portion having openings therethrough, each of said openings having a trailing edge portion on the perimeter thereof defining further cutting edges such that said milling surface extends over a surface of said flange portion.

6. A surgical milling tool according to claim 5, including a cylindrical portion interposed between said hemispherical portion and said flange portion.

7. A surgical milling tool according to claim 5, wherein the cutting edges of the flange portion lie within said surface of said flange portion.

8. A surgical milling tool according to claim 5, wherein each of said cutting edges of said flange portion is inclined at an acute angle in relation to an axial plane containing said axis and a point of said cutting edges of said flange portion.

9. A surgical milling tool according to claim 1 for milling the head of a joint, wherein the interior surface of said cup member forms said milling surface and wherein said cup member is detachably connected to a bell means, said bell means being radially spaced from and surrounding at least that portion of said cup member having said hemispherical portion of said milling surface for collecting bone shavings cut by said cutting edges and means provided on said bell means for detachably connecting the milling tool to a hand-operated milling machine.

10. A surgical milling tool according to claim 9, including an externally threaded ring connected to said cup member, said ring being threadably engageable with a threaded portion arranged at an edge of said bell means.

* * * * *